United States Patent
Durfee et al.

(10) Patent No.: US 12,396,656 B2
(45) Date of Patent: Aug. 26, 2025

(54) SYSTEMS AND METHODS FOR VISUALIZING ANATOMY, LOCATING MEDICAL DEVICES, OR PLACING MEDICAL DEVICES

(71) Applicant: Bard Access Systems, Inc., Salt Lake City, UT (US)

(72) Inventors: Tyler L. Durfee, Stansbury, UT (US); Eddie K. Burnside, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 1026 days.

(21) Appl. No.: 16/209,601

(22) Filed: Dec. 4, 2018

(65) Prior Publication Data

US 2019/0167148 A1 Jun. 6, 2019

Related U.S. Application Data

(60) Provisional application No. 62/594,454, filed on Dec. 4, 2017.

(51) Int. Cl.
*A61B 5/06* (2006.01)
*A61B 34/00* (2016.01)
(Continued)

(52) U.S. Cl.
CPC .............. *A61B 5/062* (2013.01); *A61B 34/20* (2016.02); *A61B 34/25* (2016.02); *A61B 90/36* (2016.02);
(Continued)

(58) Field of Classification Search
CPC ......... A61B 5/062; A61B 34/20; A61B 34/25; A61B 90/36; A61B 2017/00216;
(Continued)

(56) References Cited

U.S. PATENT DOCUMENTS

| 5,005,592 A | 4/1991 | Cartmell |
| 5,042,486 A | 8/1991 | Pfeiler et al. |

(Continued)

FOREIGN PATENT DOCUMENTS

| WO | WO-2007069186 A2 * | 6/2007 | ............... A61B 5/06 |
| WO | 2015144640 A1 | 10/2015 | |

(Continued)

OTHER PUBLICATIONS

PCT/US2019/035271 filed Jun. 3, 2019 International Search Report and Written Opinion dated Aug. 16, 2019.

(Continued)

*Primary Examiner* — Michae J Carey
*Assistant Examiner* — Zainab Mohammed Aldarraji
(74) *Attorney, Agent, or Firm* — Rutan & Tucker LLP

(57) ABSTRACT

A medical device-placing system includes an ultrasound probe, a medical-device detector, a console, and an alternative-reality headset. The ultrasound probe is configured to emit ultrasound signals into a patient's limb and receive echoed ultrasound signals from the patient's limb. The medical-device detector is configured for placement about the patient's limb. The console is configured to transform the echoed ultrasound signals to produce ultrasound-image segments corresponding to anatomical structures of the patient's limb, as well as transform magnetic-sensor signals from the medical-device detector into location information for a magnetized medical device within the patient's limb. The alternative-reality headset includes a display screen through which a wearer of the alternative-reality headset can see the patient's limb. The display screen is configured to display over the patient's limb a virtual medical device per the location information for the medical device within objects of virtual anatomy corresponding to the ultrasound-image segments.

18 Claims, 11 Drawing Sheets

(51) Int. Cl.
*A61B 34/20* (2016.01)
*A61B 90/00* (2016.01)
A61B 17/00 (2006.01)
A61B 34/30 (2016.01)
G02B 27/01 (2006.01)

(52) U.S. Cl.
CPC ........... *A61B 2017/00216* (2013.01); *A61B 2034/2051* (2016.02); *A61B 2034/301* (2016.02); *A61B 2090/365* (2016.02); *A61B 2562/0223* (2013.01); *G02B 27/017* (2013.01)

(58) Field of Classification Search
CPC ...... A61B 2090/365; A61B 2034/2051; A61B 2562/0223; A61B 2034/301; A61B 2090/378; G02B 27/017
See application file for complete search history.

(56) References Cited

U.S. PATENT DOCUMENTS

| | | | |
|---|---|---|---|
| 5,099,845 A | 3/1992 | Besz et al. | |
| 5,402,801 A | 4/1995 | Taylor | |
| 5,645,065 A | 7/1997 | Shapiro et al. | |
| 5,740,802 A | 4/1998 | Nafis et al. | |
| 5,776,050 A | 7/1998 | Chen et al. | |
| 6,019,725 A | 2/2000 | Vesely et al. | |
| 6,594,517 B1 | 7/2003 | Nevo | |
| 6,612,991 B2 | 9/2003 | Sauer et al. | |
| 6,695,779 B2 | 2/2004 | Sauer et al. | |
| 7,383,073 B1 | 6/2008 | Abovitz et al. | |
| 7,466,303 B2 | 12/2008 | Yi et al. | |
| 7,491,198 B2 | 2/2009 | Kockro | |
| 7,599,730 B2 | 10/2009 | Hunter et al. | |
| 7,697,972 B2 | 4/2010 | Verard et al. | |
| 7,769,422 B2* | 8/2010 | DiSilvestro | A61B 5/6828 600/407 |
| 7,831,294 B2 | 11/2010 | Viswanathan | |
| 7,873,401 B2 | 1/2011 | Shachar | |
| 7,901,358 B2* | 3/2011 | Mehi | G10K 11/346 600/447 |
| 8,116,848 B2 | 2/2012 | Shahidi | |
| 8,152,724 B2 | 4/2012 | Ridley et al. | |
| 8,401,616 B2 | 3/2013 | Verard et al. | |
| 8,483,800 B2* | 7/2013 | Jensen | G01B 7/30 600/424 |
| 8,663,120 B2 | 3/2014 | Markowitz et al. | |
| 9,251,721 B2 | 2/2016 | Lampotang et al. | |
| 9,393,080 B2 | 7/2016 | Zentgraf et al. | |
| 9,504,456 B2 | 11/2016 | Frimer et al. | |
| 9,563,266 B2 | 2/2017 | Banerjee et al. | |
| 9,566,043 B2 | 2/2017 | Kanade et al. | |
| 9,629,595 B2 | 4/2017 | Walker et al. | |
| 10,342,575 B2* | 7/2019 | Cox | A61B 5/063 |
| 2006/0073455 A1 | 4/2006 | Buyl et al. | |
| 2007/0078334 A1* | 4/2007 | Scully | A61B 5/06 600/424 |
| 2008/0309326 A1* | 12/2008 | Schechter | A61B 5/06 324/207.12 |
| 2009/0259123 A1 | 10/2009 | Navab et al. | |
| 2010/0204569 A1 | 8/2010 | Burnside et al. | |
| 2011/0015533 A1* | 1/2011 | Cox | A61B 5/283 600/509 |
| 2012/0143029 A1 | 6/2012 | Silverstein et al. | |
| 2012/0165671 A1 | 6/2012 | Hill et al. | |
| 2012/0302875 A1 | 11/2012 | Kohring | |
| 2013/0218024 A1 | 8/2013 | Boctor et al. | |
| 2014/0188133 A1 | 7/2014 | Misener | |
| 2014/0218366 A1 | 8/2014 | Kosmecki et al. | |
| 2015/0216446 A1 | 8/2015 | Bukhman et al. | |
| 2016/0000303 A1 | 1/2016 | Klein et al. | |
| 2016/0000516 A1 | 1/2016 | Cheng et al. | |
| 2016/0022125 A1 | 1/2016 | Nicolau et al. | |
| 2016/0022375 A1 | 1/2016 | Blake et al. | |
| 2016/0143693 A1 | 5/2016 | Yilmaz et al. | |
| 2016/0225192 A1* | 8/2016 | Jones | G06F 3/012 |
| 2016/0245670 A1 | 8/2016 | Nelson et al. | |
| 2016/0278869 A1* | 9/2016 | Grunwald | A61B 5/0006 |
| 2016/0302747 A1 | 10/2016 | Averbuch | |
| 2016/0320210 A1 | 11/2016 | Nelson et al. | |
| 2017/0065379 A1 | 3/2017 | Cowburn et al. | |
| 2019/0307419 A1 | 10/2019 | Durfee | |

FOREIGN PATENT DOCUMENTS

| | | |
|---|---|---|
| WO | 2015150444 A1 | 10/2015 |
| WO | 2016066287 A1 | 5/2016 |
| WO | 2016066759 A1 | 5/2016 |
| WO | 2016067092 A2 | 5/2016 |
| WO | 2019236505 A1 | 12/2019 |

OTHER PUBLICATIONS

U.S. Appl. No. 16/370,353, filed Mar. 29, 2019 Non-Final Office Action dated Apr. 9, 2021.
U.S. Appl. No. 16/430,414, filed Jun. 3, 2019 Non-Final Office Action dated May 13, 2021.

* cited by examiner

SYSTEMS AND METHODS FOR VISUALIZING ANATOMY, LOCATING MEDICAL DEVICES, OR PLACING MEDICAL DEVICES

PRIORITY

This application claims the benefit of priority to U.S. Provisional Application No. 62/594,454, filed Dec. 4, 2017, titled "Enhanced Visualization and Positioning System for an Ultrasound Imaging Device," which is incorporated by reference in its entirety into this application.

BACKGROUND

When placing a medical device in the peripheral vasculature such as the vasculature of the arms or legs, it is difficult to determine where the medical device, or a tip thereof, is at any given point in time. For example, clinicians often use fluoroscopy to track medical devices such as guidewires or catheters, but the vasculature is not visible in such X-ray-based technology, which makes it is impossible to determine exactly where the tip of a guidewire or catheter is in the vasculature. In addition, fluoroscopy exposes both patients and clinicians to ionizing radiation putting their health at risk. Therefore, an ability to visualize anatomy such as the peripheral vasculature is needed. In addition, an ability to visualize such anatomy in conjunction with medical devices such as guidewires and catheters is needed to finally make it possible to determine exactly where such medical devices are during placement thereof. Lastly, such abilities should not adversely affect patients or clinicians. Disclosed herein are systems and methods for visualizing anatomy, locating medical devices, or placing medical devices that address one or more needs such as the foregoing.

SUMMARY

Disclosed herein is a medical device-placing system including, in some embodiments, an ultrasound probe, an array of magnetic sensors, a console, and an alternative-reality headset. The ultrasound probe is configured to emit ultrasound signals into a limb of a patient and receive echoed ultrasound signals from the patient's limb by way of a piezoelectric sensor array. The array of magnetic sensors are embedded within a housing configured for placement about the patient's limb. The console has electronic circuitry including memory and a processor configured to transform the echoed ultrasound signals to produce ultrasound-image segments corresponding to anatomical structures of the patient's limb. The console is also configured to transform magnetic-sensor signals from the array of magnetic sensors into location information for a magnetized medical device within the patient's limb when the housing is placed about the patient's limb. The alternative-reality headset includes a display screen coupled to a frame having electronic circuitry including memory and a processor. The display screen is configured such that a wearer of the alternative-reality headset can see the patient's limb through the display screen. The display screen is configured to display over the patient's limb a virtual medical device in accordance with the location information for the medical device within objects of virtual anatomy corresponding to the ultrasound-image segments.

In some embodiments, the ultrasound probe is configured with a pulsed-wave Doppler imaging mode for emitting and receiving the ultrasound signals. The console is configured to capture ultrasound-imaging frames in accordance with the pulsed-wave Doppler imaging mode, stitch the ultrasound-imaging frames together with a stitching algorithm, and segment the ultrasound-imaging frames or the stitched ultrasound-imaging frames into the ultrasound-image segments with an image segmentation algorithm.

In some embodiments, the console is configured to transform the ultrasound-image segments into the objects of virtual anatomy with a virtualization algorithm. The console is configured to send both the virtual medical device and the objects of virtual anatomy to the alternative-reality headset for display over the patient's limb.

In some embodiments, the alternative-reality headset is configured to anchor the virtual medical device and the objects of virtual anatomy to the patient's limb over which the virtual medical device and the objects of virtual anatomy are displayed.

In some embodiments, the alternative-reality headset further includes one or more eye-tracking cameras coupled to the frame configured to capture eye movements of the wearer. The processor of the alternative-reality headset is configured to process the eye movements with an eye-movement algorithm to identify a focus of the wearer for selecting or enhancing the objects of virtual anatomy, the virtual medical device, or both corresponding to the focus of the wearer.

In some embodiments, the alternative-reality headset further includes one or more patient-facing cameras coupled to the frame configured to capture gestures of the wearer. The processor of the alternative-reality headset is configured to process the gestures with a gesture-command algorithm to identify gesture-based commands issued by the wearer for execution thereof by the alternative-reality headset.

In some embodiments, the alternative-reality headset further includes one or more microphones coupled to the frame configured to capture audio of the wearer. The processor of the alternative-reality headset is configured to process the audio with an audio-command algorithm to identify audio-based commands issued by the wearer for execution thereof by the alternative-reality headset.

In some embodiments, the housing is a rigid frame. Each magnetic sensor of the array of magnetic sensors is embedded within the frame and has a fixed spatial relationship to another magnetic sensor. The fixed spatial relationship is available to the console for transforming the magnetic-sensor signals from the array of magnetic sensors into the location information for the medical device.

In some embodiments, the medical device-placing system further includes a magnetic-field generator configured to generate a magnetic field. The console is configured to determine the spatial relationship of each magnetic sensor of the array of magnetic sensors to another magnetic sensor from the magnetic-sensor signals produced by the array of magnetic sensors while in the presence of the generated magnetic field. The determined spatial relationship is available to the console for subsequently transforming the magnetic-sensor signals from the array of magnetic sensors into the location information for the medical device.

Also disclosed herein is an anatomy-visualizing system including, in some embodiments, an ultrasound-imaging system and an alternative-reality headset. The ultrasound-imaging system includes an ultrasound probe and a console. The ultrasound probe is configured to emit ultrasound signals into a patient and receive echoed ultrasound signals from the patient by way of a piezoelectric sensor array. The console has electronic circuitry including memory and a processor configured to transform the echoed ultrasound signals to produce ultrasound-image segments corresponding to anatomical structures of the patient. The alternative-reality headset includes a display screen coupled to a frame having electronic circuitry including memory and a processor. The display screen is configured such that a wearer of the alternative-reality headset can see the patient through the display screen. The display screen is configured to display objects of virtual anatomy over the patient corresponding to the ultrasound-image segments.

In some embodiments, the ultrasound probe is configured with a pulsed-wave Doppler imaging mode for emitting and receiving the ultrasound signals. The console is configured to capture ultrasound-imaging frames in accordance with the pulsed-wave Doppler imaging mode, stitch the ultrasound-imaging frames together with a stitching algorithm, and segment the ultrasound-imaging frames or the stitched ultrasound-imaging frames into the ultrasound-image segments with an image segmentation algorithm.

In some embodiments, the console is configured to transform the ultrasound-image segments into the objects of virtual anatomy with a virtualization algorithm. The console is configured to send the objects of virtual anatomy to the alternative-reality headset for display over the patient.

In some embodiments, the alternative-reality headset is configured to anchor the objects of virtual anatomy to the patient over which the objects of virtual anatomy are displayed.

In some embodiments, the alternative-reality headset further includes one or more eye-tracking cameras coupled to the frame eye movements of the wearer. The processor of the alternative-reality headset is configured to process the eye movements with an eye-movement algorithm to identify a focus of the wearer for selecting or enhancing the objects of virtual anatomy corresponding to the focus of the wearer.

In some embodiments, the alternative-reality headset further includes one or more patient-facing cameras coupled to the frame configured to capture gestures of the wearer. The processor of the alternative-reality headset is configured to process the gestures with a gesture-command algorithm to identify gesture-based commands issued by the wearer for execution thereof by the alternative-reality headset.

In some embodiments, the alternative-reality headset further includes one or more microphones coupled to the frame configured to capture audio of the wearer. The processor of the alternative-reality headset is configured to process the audio with an audio-command algorithm to identify audio-based commands issued by the wearer for execution thereof by the alternative-reality headset.

Also disclosed herein is a medical device-locating system including, in some embodiments, an array of magnetic sensors embedded within a housing and a console having electronic circuitry including memory and a processor. The housing is configured for placement about a limb of a patient. The console is configured to transform magnetic-sensor signals from the array of magnetic sensors into location information for a magnetized medical device within the limb of the patient when the housing is placed about the limb of the patient.

In some embodiments, the housing is a rigid frame. Each magnetic sensor of the array of magnetic sensors is embedded within the frame and has a fixed spatial relationship to another magnetic sensor. The fixed spatial relationship is available to the console for transforming the magnetic-sensor signals from the array of magnetic sensors into the location information for the medical device.

In some embodiments, the housing is a drape. Each magnetic sensor of the array of magnetic sensors embedded is embedded within the drape and has a variable spatial relationship to another magnetic sensor depending upon how the drape is placed about the limb of the patient.

In some embodiments, the medical device-locating system further includes a magnetic-field generator configured to generate a magnetic field. The console is configured to determine the spatial relationship of each magnetic sensor of the array of magnetic sensors to another magnetic sensor from the magnetic-sensor signals produced by the array of magnetic sensors while in the presence of the generated magnetic field. The determined spatial relationship is available to the console for subsequently transforming the magnetic-sensor signals from the array of magnetic sensors into the location information for the medical device.

In some embodiments, the medical device-locating system further includes a display screen configured to depict the medical device within the limb of the patient in accordance with the location information for the medical device.

In some embodiments, the display screen is a see-through display screen coupled to a frame of an alternative-reality headset. The display screen is configured to receive from the console a virtual object corresponding to the medical device for depicting the medical device within the limb of the patient in accordance with the location information for the medical device.

Also disclosed herein is a method of a medical device-placing system including, in some embodiments, emitting ultrasound signals into a limb of a patient and receiving echoed ultrasound signals from the patient's limb by way of a piezoelectric sensor array of an ultrasound probe; transforming the echoed ultrasound signals with a console having electronic circuitry including memory and a processor to produce ultrasound-image segments corresponding to anatomical structures of the patient's limb; transforming magnetic-sensor signals from an array of magnetic sensors embedded within a housing placed about the patient's limb with the console into location information for a magnetized medical device within the patient's limb; displaying over the patient's limb on a see-through display screen of an alternative-reality headset having electronic circuitry including memory and a processor in a frame coupled to the display screen a virtual medical device in accordance with the location information for the medical device within objects of virtual anatomy corresponding to the ultrasound-image segments.

In some embodiments, the method further includes capturing in the memory of the console ultrasound-imaging frames in accordance with a pulsed-wave Doppler imaging mode of the ultrasound probe while emitting and receiving the ultrasound signals; stitching the ultrasound-imaging frames together with a stitching algorithm; and segmenting the ultrasound-imaging frames or the stitched ultrasound-imaging frames into the ultrasound-image segments with an image segmentation algorithm.

In some embodiments, the method further includes transforming the ultrasound-image segments into the objects of virtual anatomy with a virtualization algorithm; and sending both the virtual medical device and the objects of virtual anatomy to the alternative-reality headset for display over the patient's limb.

In some embodiments, the method further includes anchoring the virtual medical device and the objects of virtual anatomy to the patient's limb over which the virtual medical device and the objects of virtual anatomy are displayed.

In some embodiments, the method further includes capturing in the memory of the console eye movements of the wearer using one or more eye-tracking cameras coupled to the frame of the alternative-reality headset; and processing the eye movements with an eye-movement algorithm to identify a focus of the wearer for selecting or enhancing the objects of virtual anatomy corresponding to the focus of the wearer.

In some embodiments, the method further includes capturing in the memory of the console gestures of the wearer using one or more patient-facing cameras coupled to the frame of the alternative-reality headset; and processing the gestures with a gesture-command algorithm to identify gesture-based commands issued by the wearer for execution thereof by the alternative-reality headset.

In some embodiments, the method further includes capturing in the memory of the console audio of the wearer using one or more microphones coupled to the frame of the alternative-reality headset; and processing the audio with an audio-command algorithm to identify audio-based commands issued by the wearer for execution thereof by the alternative-reality headset.

In some embodiments, each magnetic sensor of the array of magnetic sensors is embedded within a rigid frame for the housing, the magnetic sensors having a fixed spatial relationship to each other.

In some embodiments, each magnetic sensor of the array of magnetic sensors is embedded within a drape for the housing, the magnetic sensors having a variable spatial relationship to each other depending upon how the drape is placed about the limb of the patient.

In some embodiments, the method further includes generating a magnetic field with a magnetic-field generator; and determining the spatial relationship of each magnetic sensor of the array of magnetic sensors to another magnetic sensor from the magnetic-sensor signals produced by the array of magnetic sensors while in the presence of the generated magnetic field.

These and other features of the concepts provided herein will become more apparent to those of skill in the art in view of the accompanying drawings and following description, which disclose particular embodiments of such concepts in greater detail.

DRAWINGS

FIG. 1 provides a block diagram for an anatomy-visualizing system in accordance with some embodiments.

FIG. 2 provides a block diagram for a medical device-locating system in accordance with some embodiments.

FIG. 3 provides a block diagram for a medical device-placing system in accordance with some embodiments.

FIG. 4 provides a block diagram for an ultrasound probe connected to a console of the anatomy-visualizing system in accordance with some embodiments.

FIG. 5 provides a block diagram for an alternative-reality headset of the anatomy-visualizing system in accordance with some embodiments.

Figure 7:
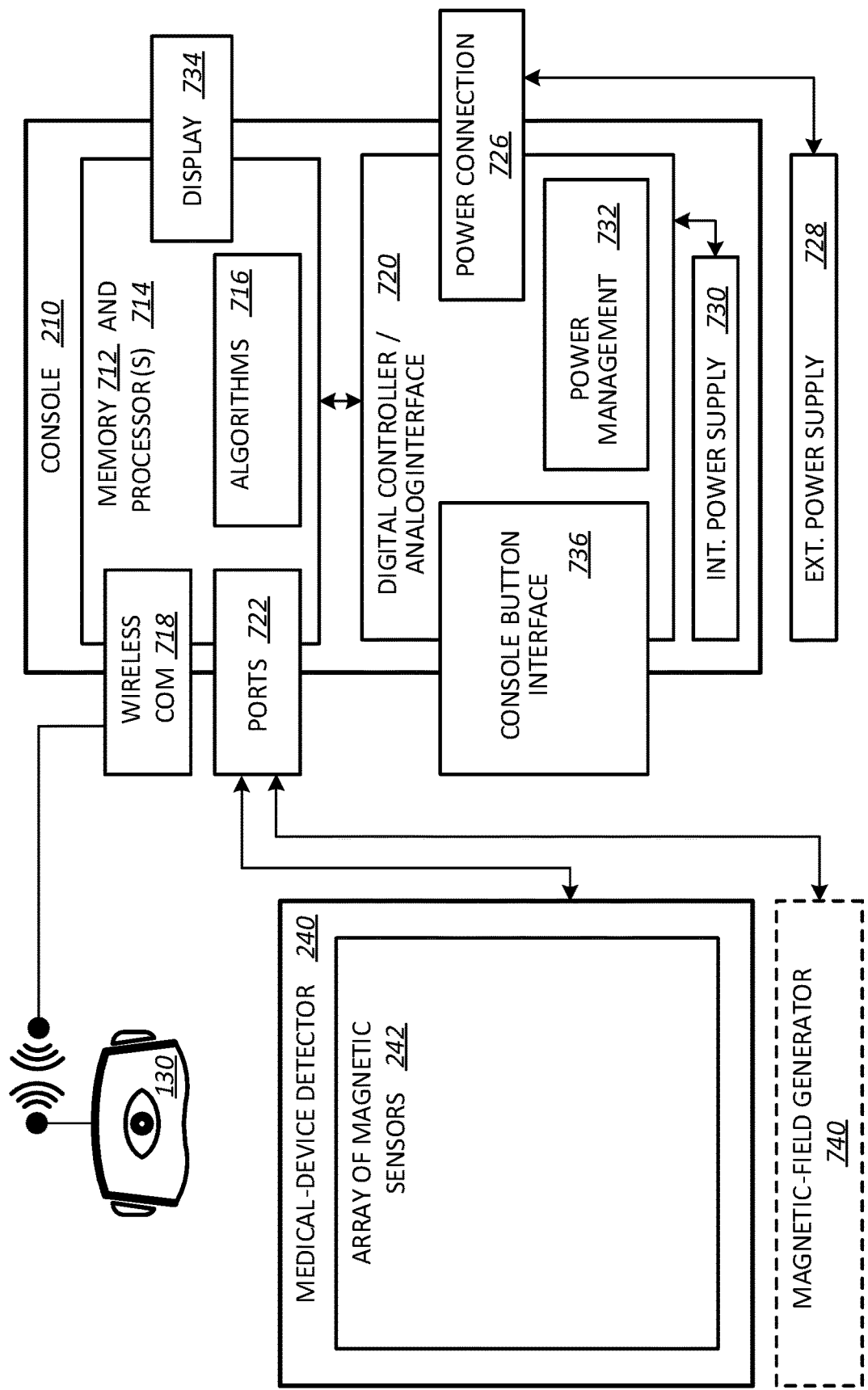

FIG. 7 provides a block diagram for a medical-device detector connected to a console of the medical device-locating system in accordance with some embodiments.

Figure 8A:
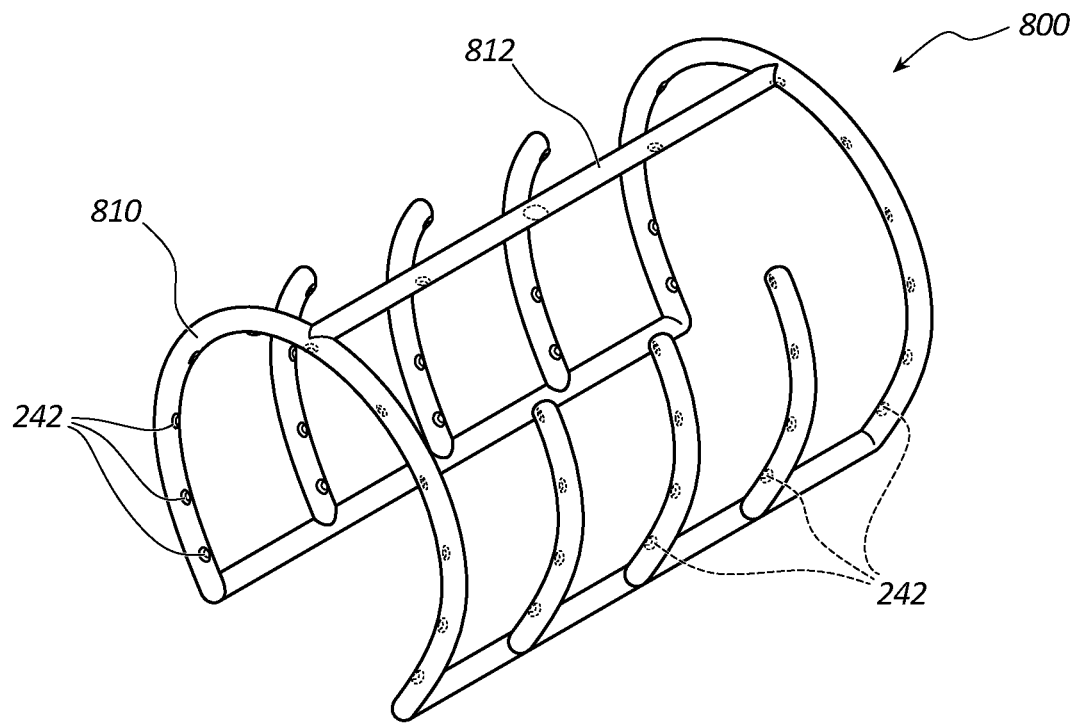

FIG. 8A provides a first medical-device detector in accordance with some embodiments.

Figure 8B:
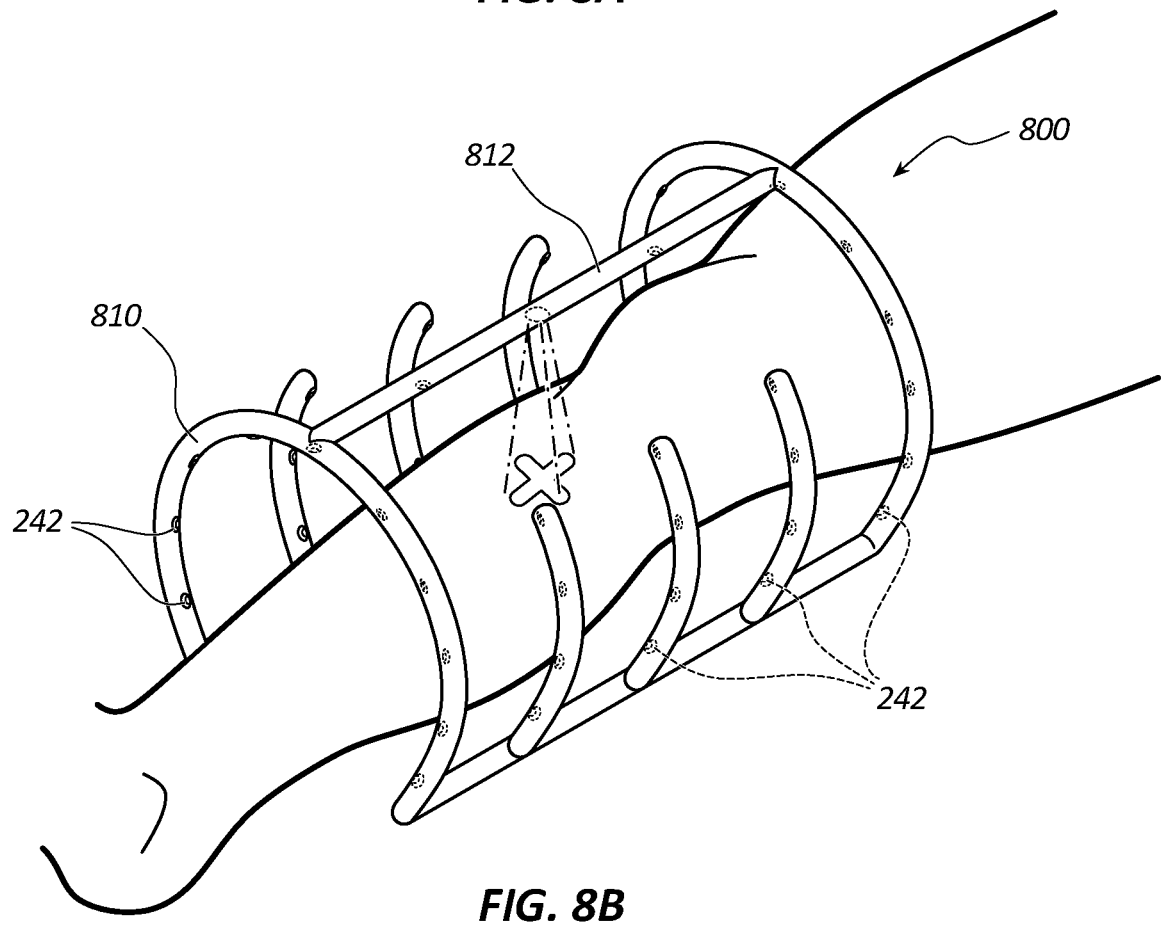

FIG. 8B provides the first medical-device detector about a limb of a patient in accordance with some embodiments.

Figure 9:
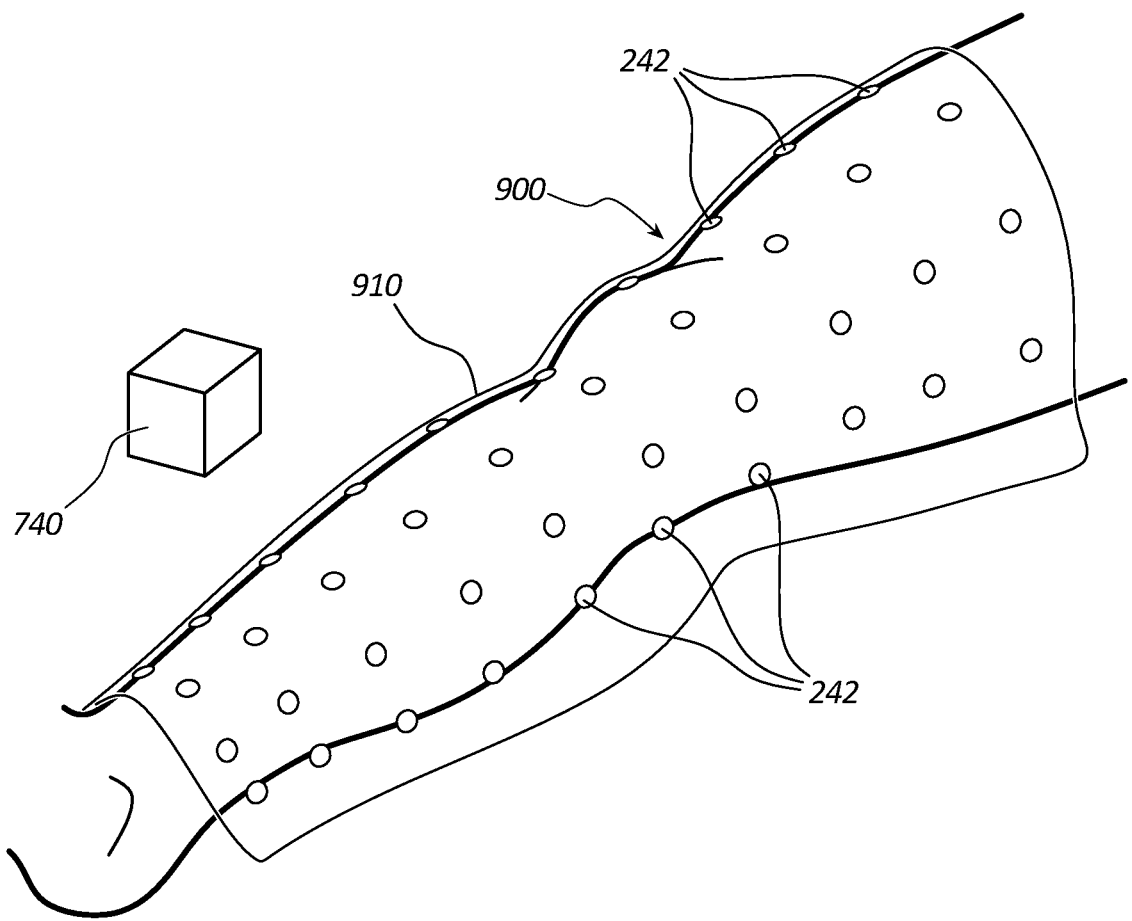

FIG. 9 provides a second medical-device detector about a limb of a patient in accordance with some embodiments.

Figure 10:
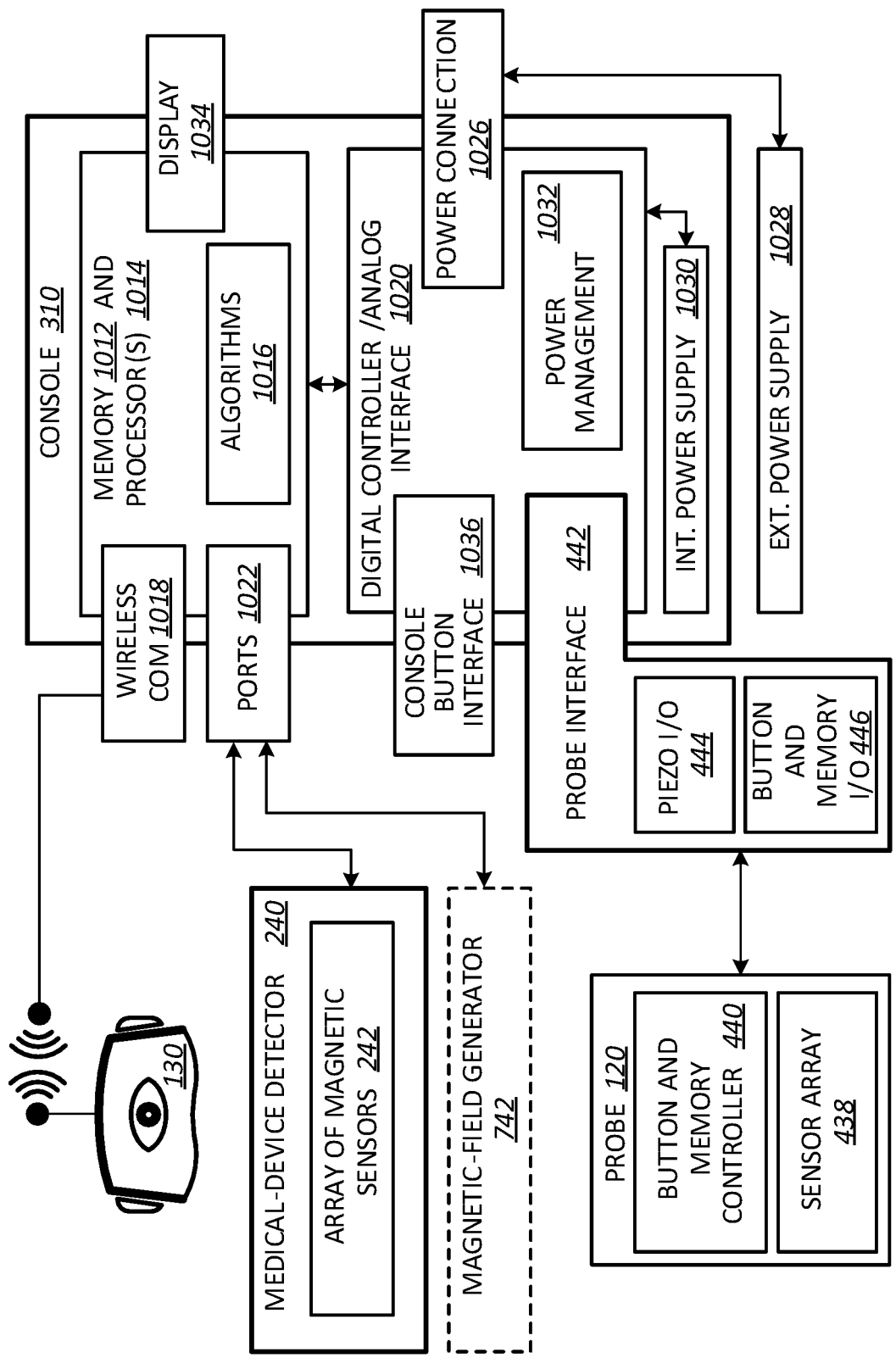

FIG. 10 provides a block diagram for an ultrasound probe and a medical-device detector connected to a console of the medical device-placing system in accordance with some embodiments.

Figure 11A:
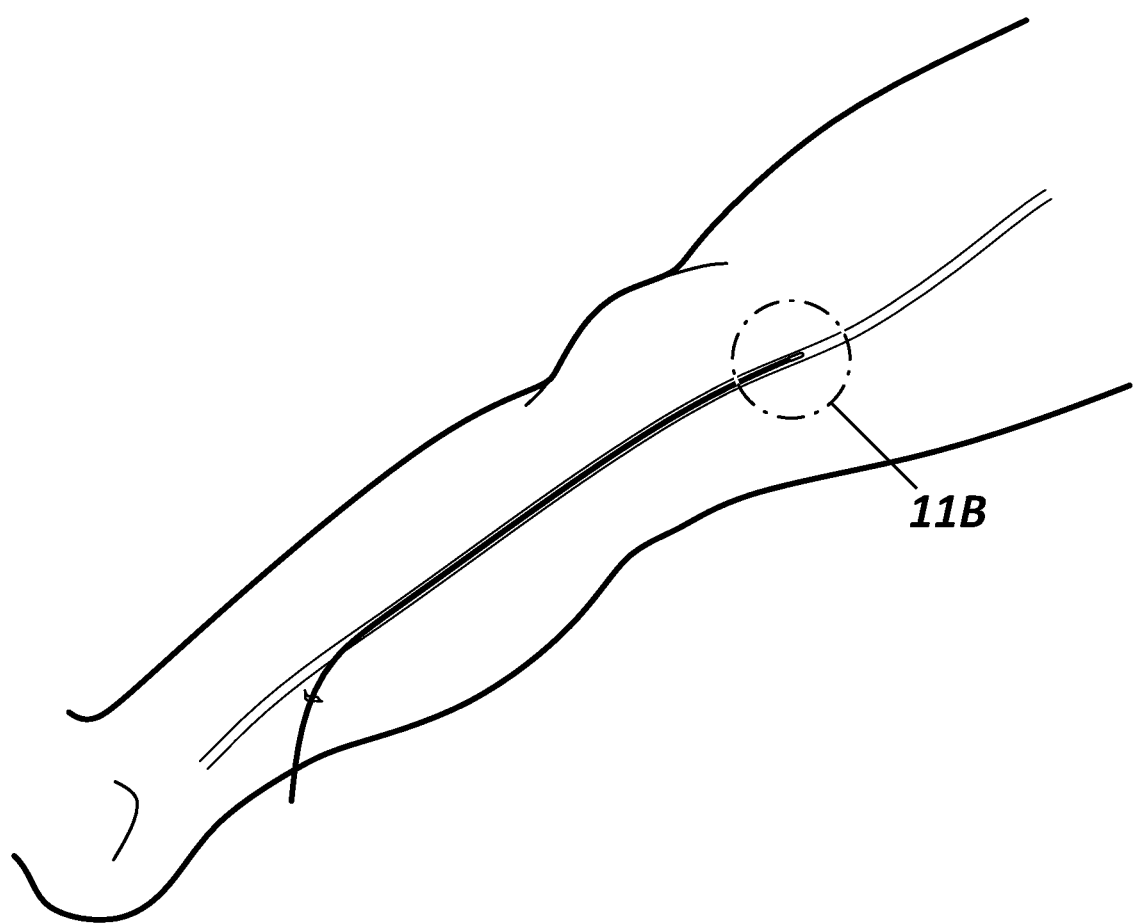

FIG. 11A illustrates objects of virtual anatomy and a virtual medical device over a patient as seen through a display screen of the alternative-reality headset in accordance with some embodiments.

Figure 11B:
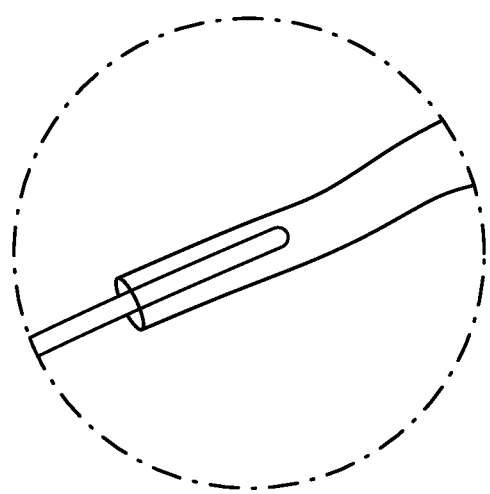

FIG. 11B illustrates a zoomed-in enhancement of the objects of virtual anatomy and the virtual medical device over the patient as seen through the display screen of the alternative-reality headset in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a medical device such as a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a medical device such as a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

With respect to "alternative reality," alternative reality includes virtual reality, augmented reality, and mixed reality unless context suggests otherwise. "Virtual reality" includes virtual content in a virtual setting, which setting can be a fantasy or a real-world simulation. "Augmented reality" and "mixed reality" include virtual content in a real-world setting. Augmented reality includes the virtual content in the real-world setting, but the virtual content is not necessarily anchored in the real-world setting. For example, the virtual content can be information overlying the real-world setting. The information can change as the real-world setting changes due to time or environmental conditions in the real-world setting, or the information can change as a result of an experiencer of the augmented reality moving through the real-world setting—but the information remains overlying the real-world setting. Mixed reality includes the virtual content anchored in every dimension of the real-world setting. For example, the virtual content can be a virtual object anchored in the real-world setting. The virtual object can change as the real-world setting changes due to time or environmental conditions in the real-world setting, or the virtual object can change to accommodate the perspective of an experiencer of the mixed reality as the experiencer moves through the real-world setting. The virtual object can also change in accordance with any interactions with the experiencer or another real-world or virtual agent. Unless the virtual object is moved to another location in the real-world setting by the experiencer of the mixed reality, or some other real-world or virtual agent, the virtual object remains anchored in the real-world setting. Mixed reality does not exclude the foregoing information overlying the real-world setting described in reference to augmented reality.

Unless defined otherwise, all technical and scientific terms used herein have the same meaning as commonly understood by those of ordinary skill in the art.

As set forth above, an ability to visualize anatomy such as the peripheral vasculature is needed. In addition, an ability to visualize such anatomy in conjunction with medical devices such as guidewires and catheters is needed to finally make it possible to determine exactly where such medical devices are during placement thereof. Lastly, such abilities should not adversely affect patients or clinicians. Disclosed herein are systems and methods for visualizing anatomy, locating medical devices, or placing medical devices that address one or more needs such as the foregoing.

Figure 1:
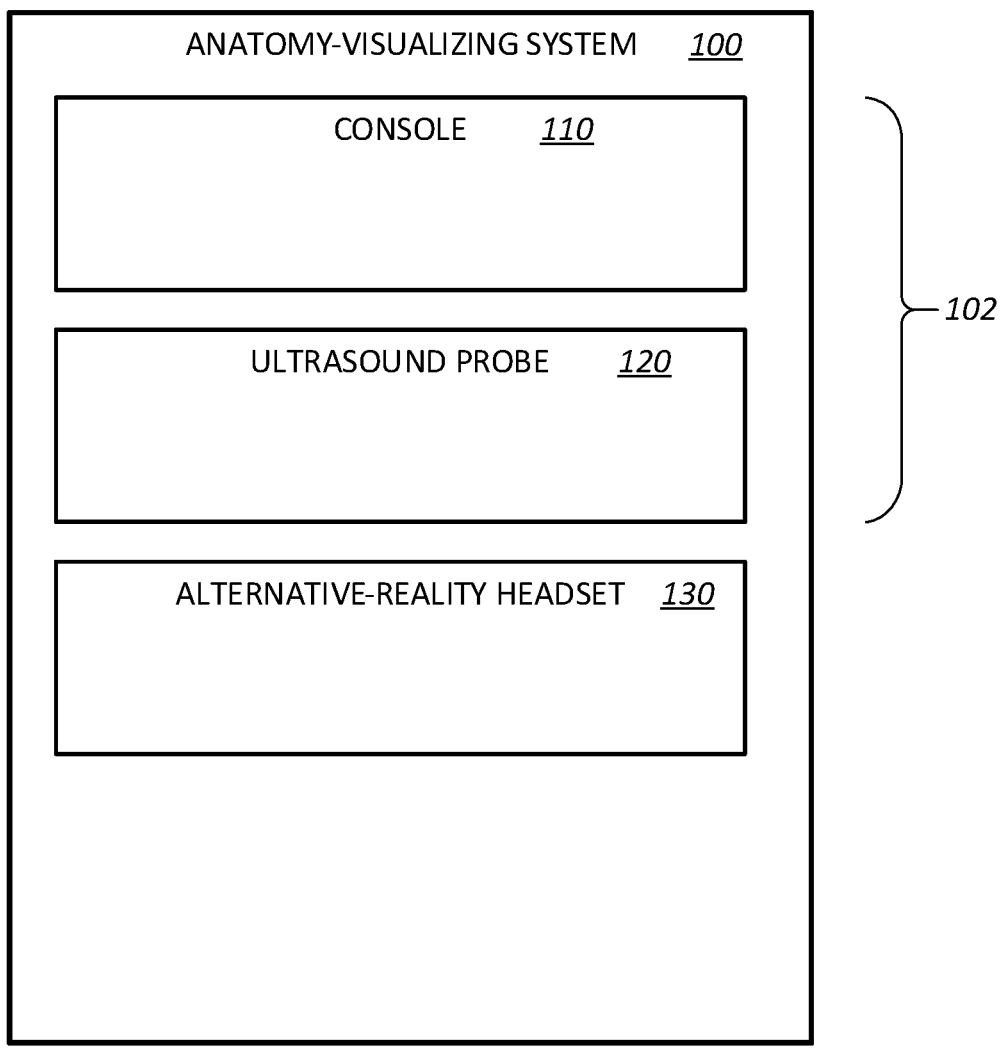
Figure 2:
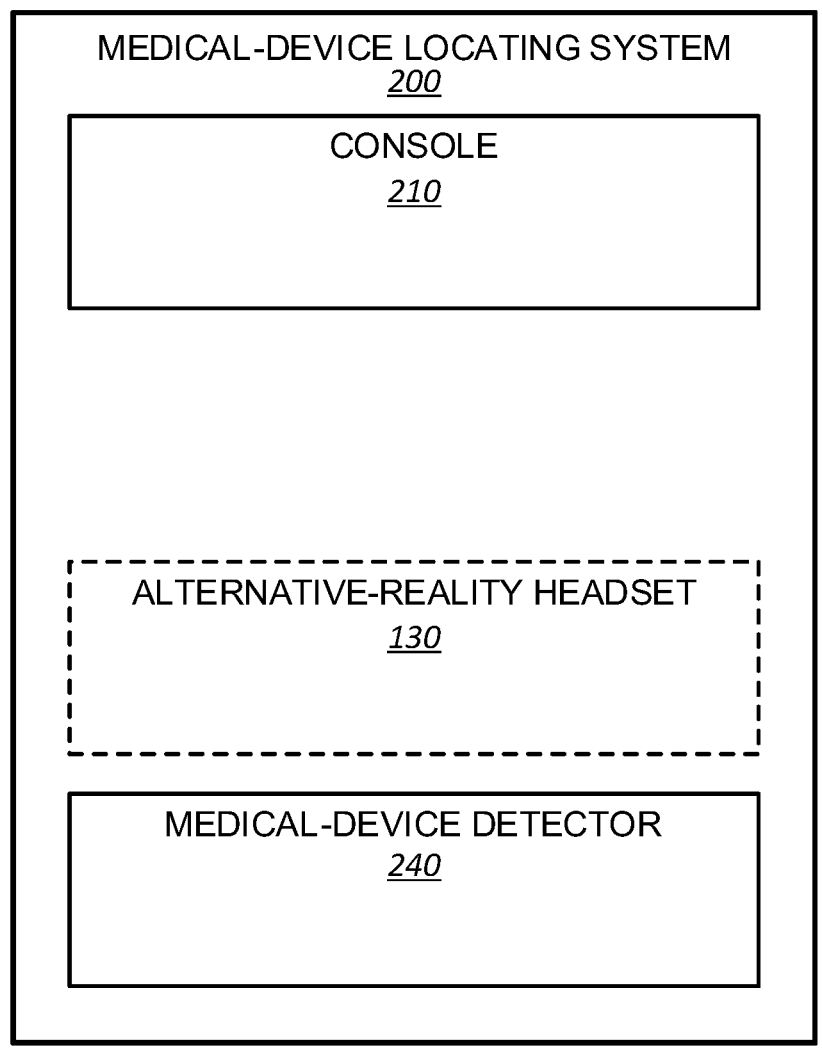
Figure 3:
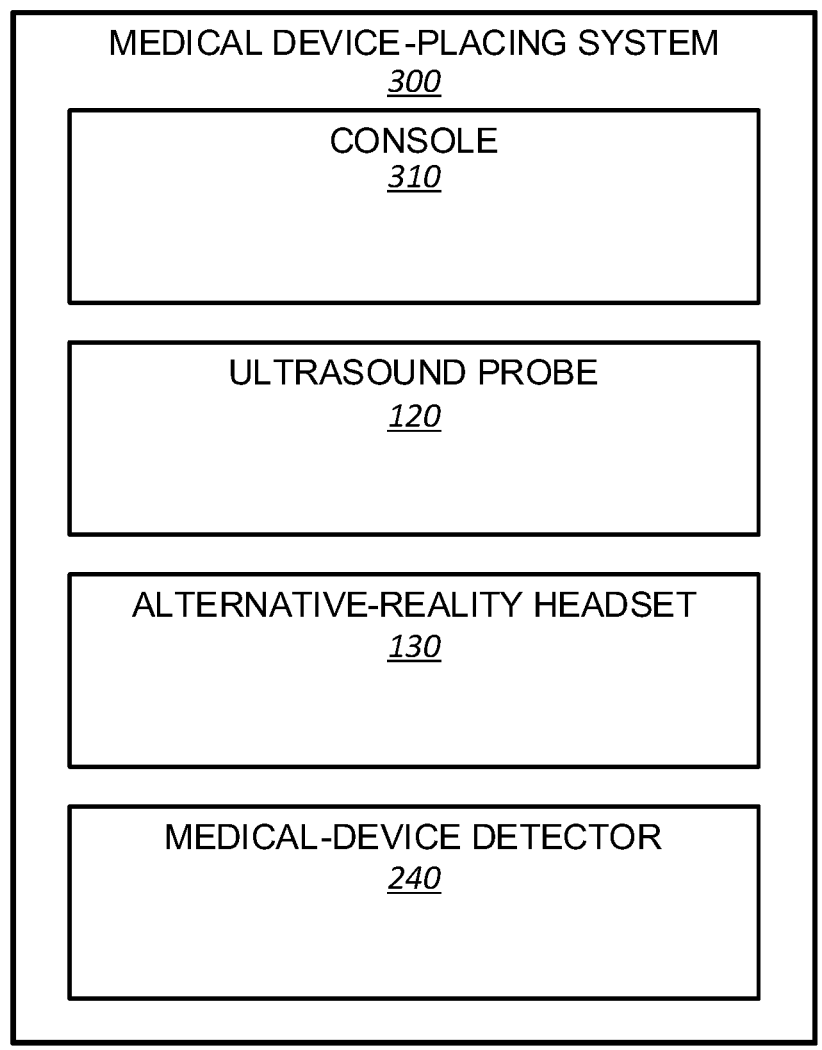

FIG. 1 provides a block diagram for an anatomy-visualizing system 100 in accordance with some embodiments. FIG. 2 provides a block diagram for a medical device-locating system 200 in accordance with some embodiments. FIG. 3 provides a block diagram for a medical device-placing system 300 in accordance with some embodiments.

As shown, the anatomy-visualizing system 100 includes an ultrasound-imaging system 102 and an alternative-reality headset 130, wherein the ultrasound-imaging system 102 includes a console 110 and an ultrasound probe 120; the medical device-locating system 200 includes a console 210, a medical-device detector 240, and, optionally, the alternative-reality headset 130; and the medical device-placing system 300 includes a console 310, the ultrasound probe 120, the alternative-reality headset 130, and the medical-device detector 240. Thus, the medical device-placing system 300 is a combination of at least some elements of the anatomy-visualizing system 100 and the medical device-locating system 200.

While each console of the consoles 110, 210, and 310 is indicated herein by a different reference numeral, the consoles 110, 120, and 130 need not be different consoles. That is, the consoles 110, 120, and 130 can be the same console. For example, that same console can be the console 310 of the medical device-placing system 300, wherein the console 310 is a combination of the console 110 of the anatomy-visualizing system 100 and the console 210 of the medical device-locating system 200. In view of the foregoing, components and functions of the console 110 described in reference to the anatomy-visualizing system 100 should be understood to apply to the anatomy-visualizing system 100 or the medical device-placing system 300. Likewise, components and functions of the console 210 described in reference to the medical device-locating system 200 should be understood to apply to the medical device-locating system 200 or the medical device-placing system 300.

Notwithstanding the foregoing, in some embodiments of the anatomy-visualizing system 100, the medical device-locating system 200, and the medical device-placing system 300 the respective consoles 110, 120, and 310 are absent. In such embodiments, the alternative reality headset 130 or another system component serves as the console or performs the functions (e.g., processing) thereof.

Anatomy-Visualizing System

Again, FIG. 1 provides the block diagram for the anatomy-visualizing system 100 in accordance with some embodiments.

As shown, the anatomy-visualizing system 100 includes the ultrasound-imaging system 102 and the alternative-reality headset 130, wherein the ultrasound-imaging system 102 includes the console 110 and the ultrasound probe 120.

Figure 4:
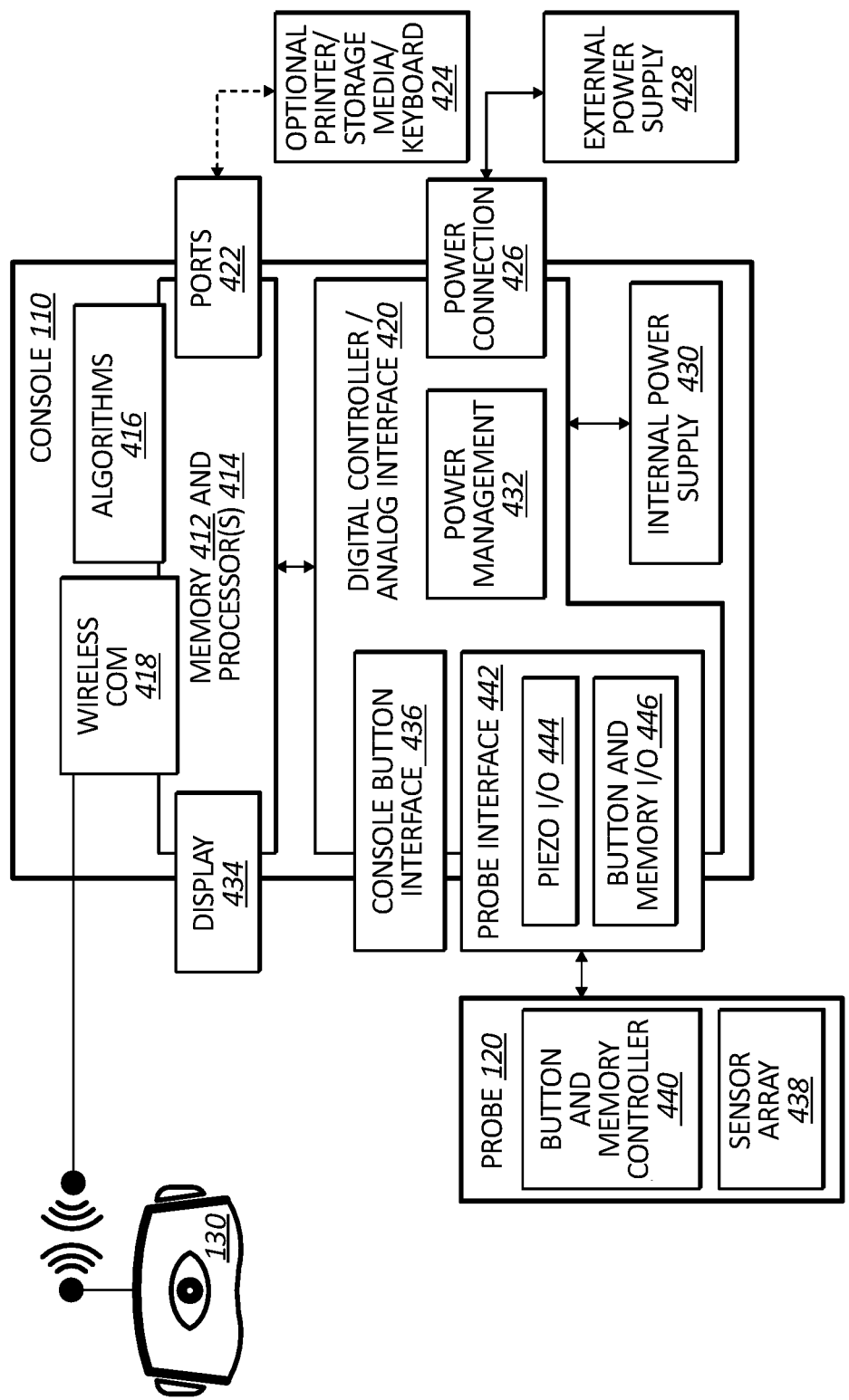

FIG. 4 provides a block diagram for the ultrasound probe 120 connected to the console of the anatomy-visualizing system 100 in accordance with some embodiments.

As shown, the console 110 has electronic circuitry including memory 412 and one or more processors 414 configured to transform echoed ultrasound signals from a patient with one or more algorithms 416 to produce ultrasound images and ultrasound-image segments therefrom corresponding to anatomical structures of the patient. The console 110 is configured to capture in the memory 412 ultrasound-imaging frames (i.e., frame-by-frame ultrasound images) in accordance with a pulsed-wave Doppler imaging mode of the ultrasound probe 120, stitch the ultrasound-imaging frames together with a stitching algorithm of the one or more algorithms 416, and segment the ultrasound-imaging frames or the stitched ultrasound-imaging frames into the ultrasound-image segments with an image segmentation algorithm of the one or more algorithms 416. The console 110 is configured to transform the ultrasound-image segments into objects of virtual anatomy with a virtualization algorithm of the one or more algorithms 416. The console 110 is configured to send the objects of virtual anatomy to the alternative-reality headset 130 for display over the patient by way of a wireless communications interface 418.

The console 110 includes a number of components of the anatomy-visualizing system 100, and the console 110 can take any form of a variety of forms to house the number of components. The one or more processors 414 and the memory 412 (e.g., non-volatile memory such as electrically erasable, programmable, read-only memory ["EEPROM"]) of the console 110 are configured for controlling various functions of the anatomy-visualizing system 100 such as executing the one or more algorithms 416 during operation of the anatomy-visualizing system 100. A digital controller or analog interface 420 is also included with the console 110, and the digital controller or analog interface 420 is in communication with the one or more processors 414 and other system components to govern interfacing between the probe 120, the alternative-reality headset 130, as well as other system components.

The console 110 further includes ports 422 for connection with additional components such as optional components 424 including a printer, storage media, keyboard, etc. The ports 422 can be universal serial bus ("USB") ports, though other ports or a combination of ports can be used, as well as other interfaces or connections described herein. A power connection 426 is included with the console 110 to enable operable connection to an external power supply 428. An internal power supply 430 (e.g., disposable or rechargeable battery) can also be employed, either with the external power supply 428 or exclusive of the external power supply 428. Power management circuitry 432 is included with the digital controller or analog interface 420 of the console 110 to regulate power use and distribution.

A display 434 can be, for example, a liquid crystal display ("LCD") integrated into the console 110 and used to display information to the clinician during a procedure. For example, the display 434 can be used to display an ultrasound image of a targeted internal body portion of the patient attained by the probe 120. Alternatively, the display 434 can be separate from the console 110 instead of integrated into the console 110; however, such a display is different than that of the alternative-reality headset 130. The console 110 can further include a console button interface 436. In combination with control buttons on the probe 120, the console button interface 436 can be used by a clinician to immediately call up a desired mode on the display 434 for use by the clinician in the procedure.

The ultrasound probe 120 is configured to emit ultrasound signals into the patient and receive the echoed ultrasound signals from the patient by way of a piezoelectric sensor array 438. The ultrasound probe 120 can be configured with a continuous wave or a pulsed-wave imaging mode. For example, the ultrasound probe 120 can configured with the foregoing pulsed-wave Doppler imaging mode for emitting and receiving the ultrasound signals.

The probe 120 further includes a button-and-memory controller 440 for governing operation of the probe 120 and buttons thereof. The button-and-memory controller 440 can include non-volatile memory such as EEPROM. The button-and-memory controller 440 is in operable communication with a probe interface 442 of the console 110, which probe interface includes a piezoelectric input-output component 444 for interfacing with the piezoelectric sensor array 438 of the probe 120 and a button-and-memory input-output component 446 for interfacing with the button-and-memory controller 440 of the probe 120.

Figure 5:
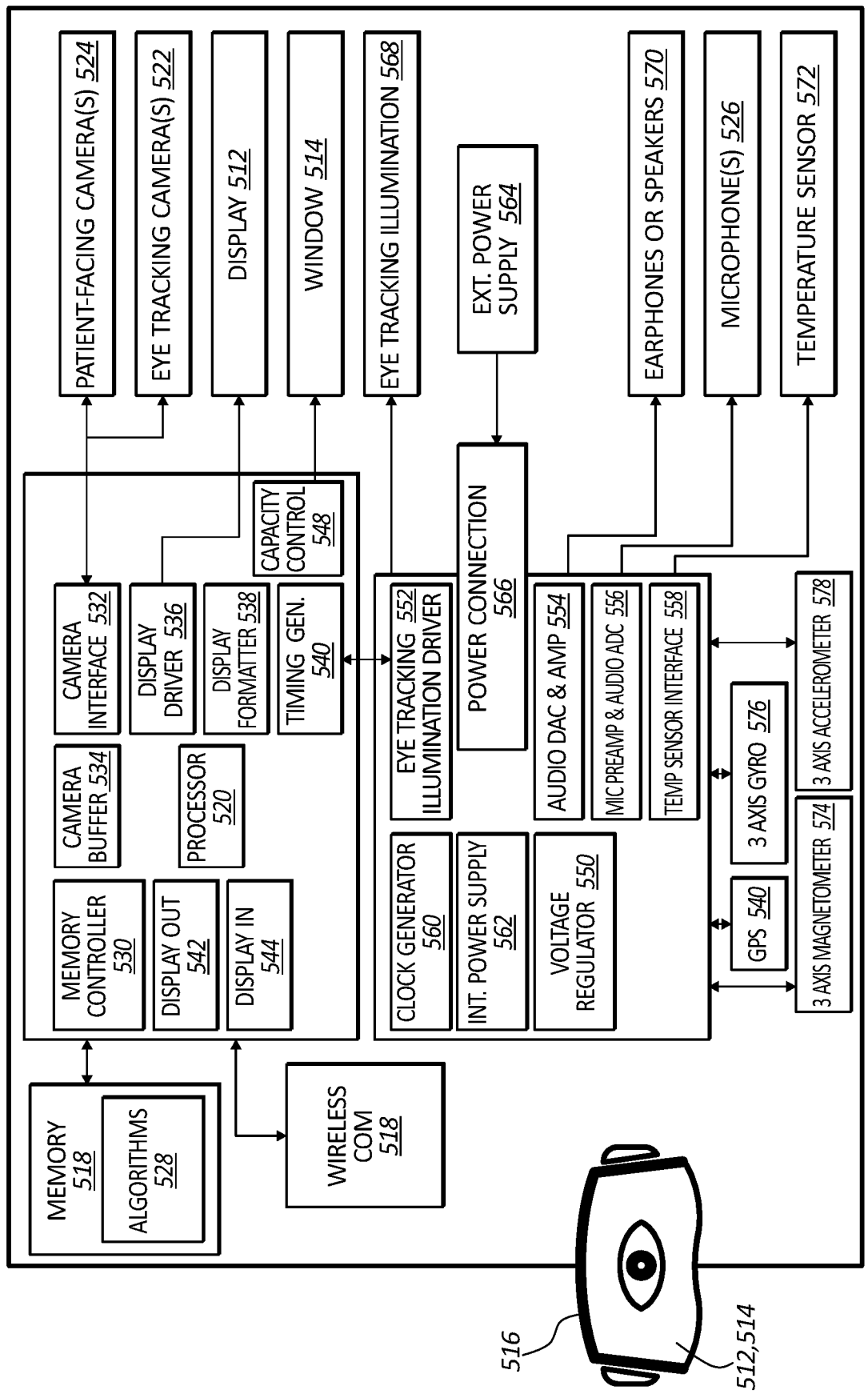

FIG. 5 provides a block diagram for the alternative-reality headset 130 of the anatomy-visualizing system 100 in accordance with some embodiments.

Figure 6A:
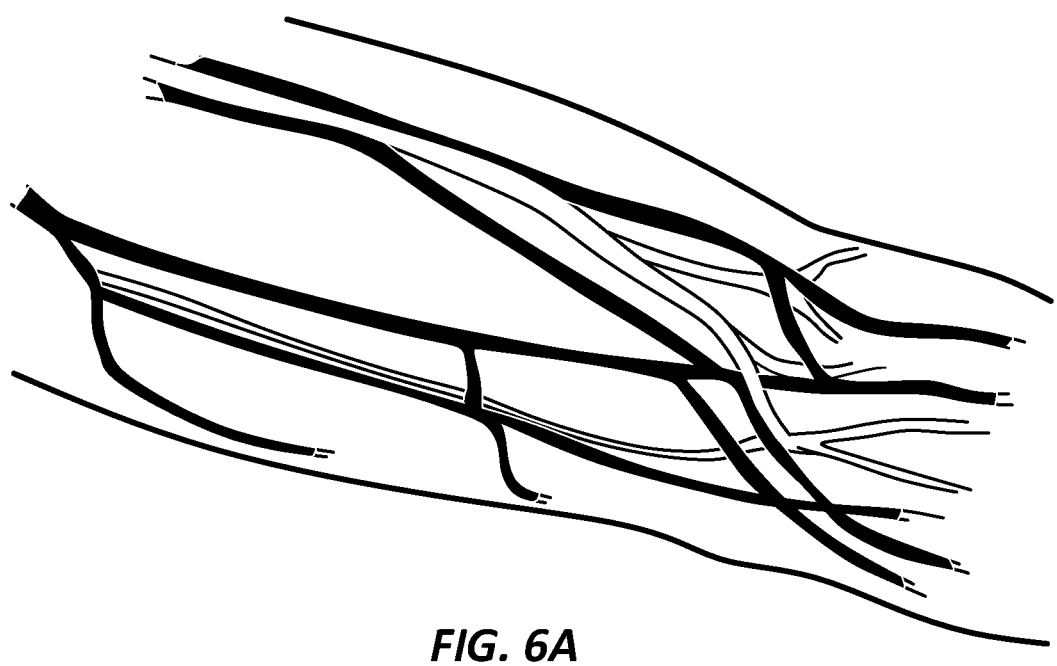
FIG. 6A illustrates objects of virtual anatomy over a patient as seen through a display screen of the alternative-reality headset in accordance with some embodiments.

As shown, the alternative-reality headset 130, which can have a goggle-type or face shield-type form factor, includes a suitably configured display screen 512 and a window 514 thereover coupled to a frame 516 having electronic circuitry including memory 518 and one or more processors 520. The display screen 512 is configured such that a wearer of the alternative-reality headset 130 can see the patient through the display screen 512 in accordance with an opacity of the window 514, which opacity is adjustable is adjustable with an opacity control 548. The display screen 512 is configured to display objects of virtual anatomy over the patient corresponding to the ultrasound-image segments produced by the console 110 with the image segmentation algorithm. (See, for example, FIG. 6A, wherein the objects of virtual anatomy correspond to vasculature in a limb of the patient.) In displaying the objects of virtual anatomy over the patient, the alternative-reality headset 130 can be configured to three-dimensionally anchor the objects of virtual anatomy to the patient over which the objects of virtual anatomy are displayed, which allows the wearer of the alternative-reality headset 130 to see a true representation of the patient's anatomy for one or more subsequent medical procedures (e.g., accessing a vessel and placing a medical device such as a guidewire of catheter in the vessel). Anchoring the objects of virtual anatomy to the patient over which the objects of virtual anatomy are displayed is characteristic of mixed reality.

The alternative-reality headset 130 can further include a perceptual user interface ("PUT") configured to enable the wearer of the alternative-reality headset 130 to interact with the alternative-reality headset 130 without a physical input device such as keyboard or mouse. Instead of a physical input device, the PUT can have input devices including, but not limited to, one or more wearer-facing eye-tracking cameras 522, one or more patient-facing cameras 524, one or more microphones 526, or a combination thereof. At least one advantage of the PUT the input devices thereof is the clinician does not have to reach outside a sterile field to execute a command of the alternative-reality headset 130.

Figure 6B:
FIG. 6B illustrates a cross-sectioned enhancement of the objects of virtual anatomy over the patient as seen through the display screen of the alternative-reality headset in accordance with some embodiments.

With respect to the one or more eye-tracking cameras 522, the one or more eye-tracking cameras 522 can be coupled to the frame 516 and configured to capture eye movements of the wearer in a camera buffer 534 or the memory 518. The processor 520 of the alternative-reality headset 130 can be configured to process the eye movements with an eye-movement algorithm of one or more algorithms 528 to identify a focus of the wearer for selecting the objects of virtual anatomy or other virtual objects (e.g., a virtual medical device) corresponding to the focus of the wearer. For example, the focus of the wearer can be used by the PUT to select an object of virtual anatomy for enhancing the object of virtual anatomy by way of highlighting the object of virtual anatomy or increasing the contrast between the object of virtual anatomy and its environment. In another example, the focus of the wearer can be used by the PUI to select an object of virtual anatomy for performing one or more other operations of the PUI such as zooming in on the object of virtual anatomy, providing a cross-section of the one or more objects of virtual anatomy, or the like. (See, for example, FIG. 6B, wherein the objects of virtual anatomy correspond to vasculature in a limb of the patient, and wherein the objects of virtual anatomy are in cross section.)

With respect to the one or more patient-facing cameras 524, the one or more patient-facing cameras 524 can be coupled to the frame 516 and configured to capture gestures of the wearer in a camera buffer 534 or the memory 518. The processor 520 of the alternative-reality headset 130 can be configured to process the gestures with a gesture-command algorithm of the one or more algorithms 528 to identify gesture-based commands issued by the wearer for execution thereof by the alternative-reality headset 130.

With respect to the one or more microphones 526, the one or more microphones 526 can be coupled to the frame 516 configured to capture audio of the wearer in the memory 518. The processor 520 of the alternative-reality headset 130 can be configured to process the audio with an audio-command algorithm of the one or more algorithms 528 to identify audio-based commands issued by the wearer for execution thereof by the alternative-reality headset 130.

The electronic circuitry includes the processor 520, a memory controller 530 in communication with the memory 518 (e.g., dynamic random-access memory ["DRAM"]), a camera interface 532, the camera buffer 534, a display driver 536, a display formatter 538, a timing generator 540, a display-out interface 542, and a display-in interface 544. Such components can be in communication with each other through the processor 520, dedicated lines of one or more buses, or a combination thereof.

The camera interface 216 is configured to provide an interface to the one or more eye-tracking cameras 522 and the one or more patient-facing cameras 524, as well as store respective images received from the cameras 522, 524 in the camera buffer 534 or the memory 518. Each camera of the one or more eye-tracking cameras 522 can be an infrared ("IR") camera or a position-sensitive detector ("PSD") configured to track eye-glint positions by way of IR reflections or eye glint-position data, respectively.

The display driver 220 is configured to drive the display 512. The display formatter 538 is configured to provide display-formatting information for the objects of virtual anatomy to the one or more processors 414 of the console 110 for formatting the objects of virtual anatomy for display on display 514 the over the patient. The timing generator 540 is configured to provide timing data for the alternative-reality headset 130. The display-out interface 542 includes a buffer for providing images from the one or more eye-tracking cameras 522 or the one or more patient-facing cameras 524 to the one or more processors 414 of the console 110. The display-in interface 544 includes a buffer for receiving images such as the objects of virtual anatomy to be displayed on the display 512. The display-out and display-in interfaces 542,544 are configured to communicate with the console 110 by way of wireless communications interface 546. The opacity control 548 is configured to change a degree of opacity of the window 514.

Additional electronic circuitry includes a voltage regulator 550, an eye-tracking illumination driver 552, an audio digital-to-analog converter ("DAC") and amplifier 554, a microphone preamplifier and audio analog-to-digital converter ("ADC") 556, a temperature-sensor interface 558, and a clock generator 560. The voltage regulator 550 is configured to receive power from an internal power supply 562 (e.g., a battery) or an external power supply 564 through power connection 566. The voltage regulator 550 is configured to provide the received power to the electronic circuitry of the alternative-reality headset 130. The eye-tracking illumination driver 236 is configured to control an eye-tracking illumination unit 568 by way of a drive current or voltage to operate about a predetermined wavelength or within a predetermined wavelength range. The audio DAC and amplifier 554 is configured to provide audio data to earphones or speakers 570. The microphone preamplifier and audio ADC 556 is configured to provide an interface for the one or more microphones 526. The temperature sensor interface 558 is configured as an interface for a temperature sensor 572. In addition, the alternative-reality headset 130 can include orientation sensors including a three-axis magnetometer 574, a three-axis gyroscope 576, and a three-axis accelerometer 578 configured to provide orientation-sensor data for determining an orientation of the alternative-reality headset 130 at any given time. Furthermore, the alternative-reality headset 130 can include a global-positioning system ("GPS") receiver 580 configured to receive GPS data (e.g., time and position information for one or more GPS satellites) for determining a location of the alternative-reality headset 130 at any given time.

Medical Device-Locating System

Again, FIG. 2 provides the block diagram for the medical device-locating system 200 in accordance with some embodiments.

As shown, the medical device-locating system 200 includes the console 210, the medical-device detector 240 including an array of magnetic sensors 242, and, optionally, the alternative-reality headset 130.

FIG. 7 provides a block diagram for the medical-device detector 240 connected to the console 210 of the medical device-locating system 200 in accordance with some embodiments.

As shown, the console 210 has electronic circuitry including memory 712 and one or more processors 714 configured to transform magnetic-sensor signals from the array of magnetic sensors 242 with one or more algorithms 716 (e.g., a location-finding algorithm including, for example, triangulation) into location information for a magnetized medical device (e.g., a catheter including a magnetic element) within a limb of a patient when the medical-device detector 240 is placed about the limb of the patient.

The console 210 includes a number of components of the medical device-locating system 200, and the console 210 can take any form of a variety of forms to house the number of components. The one or more processors 714 and the memory 712 (e.g., non-volatile memory such as EEPROM) of the console 210 are configured for controlling various functions of the medical device-locating system 200 such as executing the one or more algorithms 716 during operation of the medical device-locating system 200. A digital controller or analog interface 720 is also included with the console 210, and the digital controller or analog interface 720 is in communication with the one or more processors 714 and other system components to govern interfacing between the medical-device detector 240, the alternative-reality headset 130, as well as other system components. The console 210 can also be configured with a wireless communications interface 418 to send to the alternative-reality headset 130 location information, or a representation of the medical device (e.g., a virtual medical device) in accordance with the location information, for a magnetized medical device within a limb of a patient for display on the display 512 of the alternative-reality headset 130. (See, for example, FIGS. 11A and 11B, wherein the objects of virtual anatomy correspond to vasculature in the limb of the patient, and wherein a virtual medical device such as a guidewire or catheter is being advanced therethrough.)

The console 210 further includes ports 722 for connection with the medical-device detector 240 as well as additional, optional components such as a magnetic-field generator 740, a printer, storage media, keyboard, etc. The ports 722 can be USB ports, though other ports or a combination of ports can be used, as well as other interfaces or connections described herein. A power connection 726 is included with the console 210 to enable operable connection to an external power supply 728. An internal power supply 730 (e.g., disposable or rechargeable battery) can also be employed, either with the external power supply 728 or exclusive of the external power supply 728. Power management circuitry 732 is included with the digital controller or analog interface 720 of the console 210 to regulate power use and distribution.

A display 734 can be, for example, an LCD integrated into the console 210 and used to display information to the clinician during a procedure. For example, the display 734 can be used to display location information, or depict a representation of the medical device (e.g., virtual medical device) in accordance with the location information, for a magnetized medical device within a limb of a patient. Alternatively, the display 734 can be separate from the console 210 instead of integrated into the console 210; however, such a display is different than that of the alternative-reality headset 130, which can also be configured to display location information (e.g., as a location-information overlay), or depict a representation of the medical device (e.g., virtual medical device) in accordance with the location information, for a magnetized medical device within a limb of a patient. The console 210 can further include a console button interface 736. The console button interface 736 can be used by a clinician to immediately call up a desired mode (e.g., a mode with the magnetic-field generator 740, a mode without the magnetic-field generator 740, etc.) on the display 734 for use by the clinician in the procedure.

FIG. 8A provides a first medical-device detector 800 in accordance with some embodiments. FIG. 8B provides the first medical-device detector 800 about a limb of a patient in accordance with some embodiments. FIG. 9 provides a second medical-device detector 900 about a limb of a patient in accordance with some embodiments.

As shown, each medical-device detector of the first medical-device detector 800 and the second medical-device detector 900 includes the array of magnetic sensors 242 embedded within a housing 810, 910 configured for placement about a limb (e.g., an arm or a leg) of a patient. The console 210 is configured to transform magnetic-sensor signals from the array of magnetic sensors 242 with the one or more algorithms 716 (e.g., a location-finding algorithm) into location information, or the representation of the medical device (e.g., virtual medical device) in accordance with the location information, for a magnetized medical device within the limb of the patient when the medical-device detector 800, 900 is placed about the limb of the patient.

The housing 810 of the first medical-device detector 800 is a rigid frame. Each magnetic sensor of the array of magnetic sensors 242 embedded within the frame has a fixed spatial relationship to another magnetic sensor. The fixed spatial relationship is communicated to the console 210 upon connecting the first medical-device detector 800 to a port of the ports 722 of the console 210 or calling up one or more modes with the console button interface 736 of the console 210 for using the first medical-device detector 800 without the magnetic-field generator 740. Using the fixed spatial relationship of the array of magnetic sensors 242 in the first medical-device detector 800, the console 210 is able to transform the magnetic-sensor signals from the array of magnetic sensors 242 into the location information, or the representation of the medical device (e.g., virtual medical device) in accordance with the location information, for the magnetized medical device within the limb of the patient.

The housing 810 of the first medical-device detector 800 can further include one or more light-emitting diodes ("LEDs") or lasers embedded within the frame such as within a strut 812 of the frame. The one or more LEDs or lasers can be configured to illuminate the limb of the patient about which the first medical-device detector 800 is placed, or the one or more LEDs or lasers can be configured to illuminate just a portion of the limb of the patient. The portion of the limb of the patient can be the portion under which a tip of the medical device is located within the limb of the patient. (See, for example, FIG. 8B, wherein the 'X' indicates illumination of just a portion of the limb of the patient under which the tip of the medical device is located.) As such, the one or more LEDs or lasers can function as a real-world light-based pointing system for identifying a medical device's location. The light-based pointing system can be used in conjunction with the alternative-reality headset 130 for confirmation of a medical device's location as the illumination provided by the light-based pointing system is visible through the see-through display 512 of the alternative-reality headset 130.

The housing 910 of the second medical-device detector 900 is a drape. Each magnetic sensor of the array of magnetic sensors 242 embedded within the drape has a variable spatial relationship to another magnetic sensor depending upon how the drape is placed about the limb of the patient. For this reason, the medical device-locating system 200 can further include the magnetic-field generator 740, which is configured to generate a magnetic field about the second medical-device detector 900 for determining the spatial relationship of one magnetic sensor of the array of magnetic sensors 242 to another magnetic sensor. Each magnetic sensor present in the array of magnetic sensors 242 is communicated to the console 210 upon connecting the second medical-device detector 900 to a port of the ports 722 of the console 210 or calling up one or more modes with the console button interface 736 of the console 210 for using the second medical-device detector 900 with the magnetic-field generator 740. With each magnetic sensor of the array of magnetic sensors 424 known, the console 210 is configured to determine the spatial relationship of each magnetic sensor to another magnetic sensor from the magnetic-sensor signals produced by the array of magnetic sensors 242 while in the presence of the generated magnetic field. This is made possible, in part due to each magnetic sensor of the array of magnetic sensors 424 being in a unique magnetic environment with respect to at least the strength and orientation of the generated magnetic field. Using the determined spatial relationship of the array of magnetic sensors 242 in the second medical-device detector 900, the console 210 is able to transform the magnetic-sensor signals from the array of magnetic sensors 242 into the location information, or the representation of the medical device (e.g., virtual medical device) in accordance with the location information, for the magnetized medical device within the limb of the patient. To ensure accuracy, the determined spatial relationship of the array of magnetic sensors 242 can be periodically confirmed in the presence of a newly generated magnetic field considering the medical device within the limb of the patient.

Medical Device-Placing System

Again, FIG. 3 provides the block diagram for the medical device-placing system 300 in accordance with some embodiments.

As shown, the medical device-placing system 300 can include the ultrasound probe 120 of the anatomy-visualizing system 100, the medical-device detector 240 including the array of magnetic sensors 242 of the medical device-locating system 200, the alternative-reality headset 130, and the console 310, which includes electronic circuitry like that of both console 110 and console 210. However, in some embodiments, other medical device-detecting technologies can be used instead of the medical device-locating system 200 such as the tip-location system ("TLS") of WO 2014/062728, which publication is incorporated by reference in its entirety into this application.

FIG. 10 provides a block diagram for the ultrasound probe 120 and the medical-device detector 240 connected to the console 310 of the medical device-placing system 300 in accordance with some embodiments.

As shown, the console 310 has electronic circuitry including memory 1012 and one or more processors 1014. Like the console 110, the console 310 is configured to transform echoed ultrasound signals from a patient with one or more algorithms 1016 to produce ultrasound images and ultrasound-image segments therefrom corresponding to anatomical structures of the patient. The console 310 is configured to capture in the memory 1012 ultrasound-imaging frames in accordance with a pulsed-wave Doppler imaging mode of the ultrasound probe 120, stitch the ultrasound-imaging frames together with a stitching algorithm of the one or more algorithms 1016, and segment the ultrasound-imaging frames or the stitched ultrasound-imaging frames into the ultrasound-image segments with an image segmentation algorithm of the one or more algorithms 1016. The console 310 is configured to transform the ultrasound-image segments into objects of virtual anatomy with a virtualization algorithm of the one or more algorithms 1016. And like the console 210, the console 310 is configured to transform magnetic-sensor signals from the array of magnetic sensors 242 with one or more algorithms 1016 (e.g., a location-finding algorithm) into location information for a magnetized medical device within a limb of the patient when the medical-device detector 240 is placed about the limb of the patient. The console 310 is configured to send to the alternative-reality headset 130 by way of a wireless communications interface 1018 both the objects of virtual anatomy and a representation of the medical device (e.g., virtual medical device) within the limb of the patient, in accordance with the location information, for display over the patient on the display 512 of the alternative-reality headset 130. In displaying the objects of virtual anatomy and the representation of the medical device over the patient, the alternative-reality headset 130 can be configured to anchor the objects of virtual anatomy and the representation of the medical device to the patient, which is characteristic of mixed reality.

The console 310 includes a number of components of the medical device-placing system 300, and the console 310 can take any form of a variety of forms to house the number of components. The one or more processors 1014 and the memory 1012 (e.g., non-volatile memory such as EEPROM) of the console 310 are configured for controlling various functions of the medical device-placing system 300 such as executing the one or more algorithms 1016 during operation of the medical device-placing system 300. A digital controller or analog interface 1020 is also included with the console 310, and the digital controller or analog interface 1020 is in communication with the one or more processors 1014 and other system components to govern interfacing between the probe 120, the medical-device detector 240, the alternative-reality headset 130, as well as other system components.

The console 210 further includes ports 1022 for connection with the medical-device detector 240 as well as additional, optional components such as the magnetic-field generator 740 or the optional components 424 (e.g., a printer, storage media, keyboard, etc.). The ports 1022 can be USB ports, though other ports or a combination of ports can be used, as well as other interfaces or connections described herein. A power connection 1026 is included with the console 310 to enable operable connection to an external power supply 1028. An internal power supply 1030 (e.g., disposable or rechargeable battery) can also be employed, either with the external power supply 1028 or exclusive of the external power supply 1028. Power management circuitry 1032 is included with the digital controller or analog interface 1020 of the console 310 to regulate power use and distribution.

A display 1034 can be, for example, an LCD integrated into the console 310 and used to display information to the clinician during a procedure. For example, the console 310 can be used to display an ultrasound image of a targeted internal body portion of the patient attained by the probe 120, the location information for a medical device within a limb of the patient, or a representation of the medical device (e.g., virtual medical device) in accordance with the location information for the medical device within the limb of the patient. Alternatively, the display 1034 can be separate from the console 310 instead of integrated into the console 310; however, such a display is different than that of the alternative-reality headset 130, which can also be configured to display the objects of virtual anatomy and the representation of the medical device (e.g., virtual medical device) within the limb of the patient.

The console 310 can further include a console button interface 1036. In combination with control buttons on the probe 120, the console button interface 1036 can be used by a clinician to immediately call up a desired ultrasound-imaging mode (e.g., a continuous wave imaging mode or a pulsed-wave imaging mode) on the display 1034 for use by the clinician in the procedure. The console button interface 1036 can be used by the clinician to immediately call up a desired medical device-locating mode (e.g., a mode with the magnetic-field generator 740, a mode without the magnetic-field generator 740, etc.) on the display 734 for use by the clinician in the procedure.

With respect to the ultrasound probe 120 and the alternative-reality headset 130 of the medical device-placing system 300, reference should be made to the description of the ultrasound probe 120 and the alternative-reality headset 130 provided for the anatomy-visualizing system 100. With respect to the medical-device detector 240 and the magnetic-field generator 742 of the medical device-placing system 300, reference should be made to the description of the medical-device detector 240 and the magnetic-field generator 742 provided for the medical device-locating system 200.

Methods

Methods of the medical device-placing system 300 incorporate methods of both the anatomy-visualizing system 100 and the medical device-locating system 200, which methods are discernable by references to the anatomy-visualizing system 100, the medical device-locating system 200, or the components thereof (e.g., the ultrasound probe 120, the medical-device detector 240, etc.) below.

Methods of the medical device-placing system 300 include emitting ultrasound signals into a limb of a patient and receiving echoed ultrasound signals from the patient's limb by way of the piezoelectric sensor array 438 of the ultrasound probe 120; transforming the echoed ultrasound signals with the console 310 having the electronic circuitry including the memory 1012, the one or more algorithms 1016, and the one or more processors 1014 to produce ultrasound-image segments corresponding to anatomical structures of the patient's limb; inserting a magnetized medical device into the patient's limb and transforming magnetic-sensor signals from the array of magnetic sensors 242 embedded within the housing 810, 910 placed about the patient's limb with the one or more algorithms 1016 (e.g., a location-finding algorithm) of the console 310 into location information for the medical device within the patient's limb; displaying over the patient's limb on the see-through display screen 512 of the alternative-reality headset 130 having the electronic circuitry including the memory 518 and the one or more processors 520 in the frame 516 coupled to the display screen 512 a virtual medical device in accordance with the location information for the medical device within objects of virtual anatomy corresponding to the ultrasound-image segments. Ultrasound imaging to produce the objects of virtual anatomy can be done at any time before inserting the medical device into the patient's limb, and the objects of virtual anatomy can be stored for later use in the memory 1012 of the console 310 or a storage medium connected to a port of the console 310.

The method can further includes capturing in the memory 1012 of the console 310 ultrasound-imaging frames in accordance with the pulsed-wave Doppler imaging mode of the ultrasound probe 120 while emitting and receiving the ultrasound signals; stitching the ultrasound-imaging frames together with the stitching algorithm of the one or more algorithms 1016; and segmenting the ultrasound-imaging frames or the stitched ultrasound-imaging frames into the ultrasound-image segments with the image segmentation algorithm of the one or more algorithms 1016.

The method can further includes transforming the ultrasound-image segments into the objects of virtual anatomy with the virtualization algorithm of the one or more algorithms 1016; and sending both the virtual medical device and the objects of virtual anatomy to the alternative-reality headset 130 for display over the patient's limb.

The method can further includes anchoring the virtual medical device and the objects of virtual anatomy to the patient's limb over which the virtual medical device and the objects of virtual anatomy are displayed.

The method can further includes capturing in the memory 1012 of the console 310 eye movements of the wearer using the one or more eye-tracking cameras 522 coupled to the frame 516 of the alternative-reality headset 130; and processing the eye movements with the eye-movement algorithm of the one or more algorithms 528 to identify a focus of the wearer for selecting or enhancing the objects of virtual anatomy corresponding to the focus of the wearer.

The method can further includes capturing in the memory 1012 of the console 310 gestures of the wearer using one or more patient-facing cameras 524 coupled to the frame 516 of the alternative-reality headset 130; and processing the gestures with the gesture-command algorithm of the one or more algorithms 528 to identify gesture-based commands issued by the wearer for execution thereof by the alternative-reality headset 130.

The method can further includes capturing in the memory 1012 of the console 310 audio of the wearer using the one or more microphones 526 coupled to the frame 516 of the alternative-reality headset 130; and processing the audio with the audio-command algorithm of the one or more algorithms 528 to identify audio-based commands issued by the wearer for execution thereof by the alternative-reality headset 130.

The method can further include generating a magnetic field with the magnetic-field generator 740; and determining a spatial relationship of each magnetic sensor of the array of magnetic sensors 242 to another magnetic sensor from the magnetic-sensor signals produced by the array of magnetic sensors 242 while in the presence of the generated magnetic field. Determining the spatial relationship of each magnetic sensor to another magnetic sensor in the array of magnetic sensors 242 is important when the array of magnetic sensors 242 is embedded within the housing 910 (e.g., a drape), for the magnetic sensors have a variable spatial relationship to each other depending upon how the housing 910 is placed about the limb of the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical device-placing system, comprising:
an ultrasound probe configured to emit ultrasound signals into a limb of a patient and receive informational signals from the limb of the patient;
an array of magnetic sensors embedded within a rigid housing configured for surrounding the limb of the patient in a plurality of planes;
a console having console electronic circuitry including memory and a processor configured to:
transform the informational signals to produce ultrasound-image segments corresponding to anatomical structures of the limb of the patient, and
transform magnetic-sensor signals from the array of magnetic sensors into location information for a magnetized medical device within the limb of the patient when the rigid housing is placed about the limb of the patient; and
an alternative-reality headset, including:
a frame having frame electronic circuitry including memory and a processor; and
a display screen coupled to the frame through which a wearer of the alternative-reality headset can see the limb of the patient, the display screen configured to display over the limb of the patient a virtual medical device in accordance with the location information for the virtual medical device within objects of virtual anatomy corresponding to the ultrasound-image segments.

2. The medical device-placing system according to claim 1, wherein the ultrasound probe is configured with a pulsed-wave Doppler imaging mode for emitting the ultrasound signals and receiving the informational signals, and wherein the console is configured to capture ultrasound-imaging frames in accordance with the pulsed-wave Doppler imaging mode, stitch the ultrasound-imaging frames together with a stitching algorithm, and segment the ultrasound-imaging frames or the stitched ultrasound-imaging frames into the ultrasound-image segments with an image segmentation algorithm.

3. The medical device-placing system according to claim 1, wherein the console is configured to transform the ultrasound-image segments into the objects of virtual anatomy with a virtualization algorithm and send both the virtual medical device and the objects of virtual anatomy to the alternative-reality headset for display over the limb of the patient.

4. The medical device-placing system according to claim 1, wherein the alternative-reality headset is configured to anchor the virtual medical device and the objects of virtual anatomy to the limb of the patient over which the virtual medical device and the objects of virtual anatomy are displayed.

5. The medical device-placing system according to claim 1, the alternative-reality headset further comprising one or more eye-tracking cameras coupled to the frame configured to capture eye movements of the wearer, the processor of the alternative-reality headset configured to process the eye movements with an eye-movement algorithm to identify a focus of the wearer for selecting or enhancing the objects of virtual anatomy, the virtual medical device, or both corresponding to the focus of the wearer.

6. The medical device-placing system according to claim 1, the alternative-reality headset further comprising one or more patient-facing cameras coupled to the frame configured to capture gestures of the wearer, the processor of the alternative-reality headset configured to process the gestures with a gesture-command algorithm to identify gesture-based commands issued by the wearer for execution thereof by the alternative-reality headset.

7. The medical device-placing system according to claim 1, the alternative-reality headset further comprising one or more microphones coupled to the frame configured to capture audio of the wearer, the processor of the alternative-reality headset configured to process the audio with an audio-command algorithm to identify audio-based commands issued by the wearer for execution thereof by the alternative-reality headset.

8. The medical device-placing system according to claim 1, wherein each magnetic sensor of the array of magnetic sensors embedded within the rigid housing has a fixed spatial relationship to another magnetic sensor available to the console for transforming the magnetic-sensor signals from the array of magnetic sensors into the location information for the virtual medical device.

9. The medical device-placing system according to claim 8, further comprising a magnetic-field generator configured to generate a magnetic field, the console configured to determine the fixed spatial relationship of each magnetic sensor of the array of magnetic sensors to another magnetic sensor from the magnetic-sensor signals produced by the array of magnetic sensors while in the presence of the generated magnetic field, thereby making a determined spatial relationship available to the console for subsequently transforming the magnetic-sensor signals from the array of magnetic sensors into the location information for the virtual medical device.

10. A method of a medical device-placing system, comprising:
emitting ultrasound signals into a limb of a patient and receiving informational signals from the limb of the patient by way of an ultrasound probe;
transforming the informational signals with a console having electronic circuitry including memory and a processor to produce ultrasound-image segments corresponding to anatomical structures of the limb of the patient;
transforming magnetic-sensor signals from an array of magnetic sensors embedded within a rigid housing surrounding the limb of the patient in a plurality of planes with the console into location information for a magnetized medical device within the limb of the patient; and
displaying over the limb of the patient on a see-through display screen of an alternative-reality headset having electronic circuitry including memory and the processor in a frame coupled to the display screen a virtual medical device in accordance with the location information for the virtual medical device within objects of virtual anatomy corresponding to the ultrasound-image segments.

11. The method according to claim 10, further comprising:
capturing, in the memory of the console, ultrasound-imaging frames in accordance with a pulsed-wave Doppler imaging mode of the ultrasound probe while emitting the ultrasound signals and receiving the informational signals;
stitching the ultrasound-imaging frames together with a stitching algorithm; and
segmenting the ultrasound-imaging frames or the stitched ultrasound-imaging frames into the ultrasound-image segments with an image segmentation algorithm.

12. The method according to claim 10, further comprising:
transforming the ultrasound-image segments into the objects of virtual anatomy with a virtualization algorithm; and
sending both the virtual medical device and the objects of virtual anatomy to the alternative-reality headset for display over the limb of the patient.

13. The method according to claim 12, further comprising anchoring the virtual medical device and the objects of virtual anatomy to the limb of the patient over which the virtual medical device and the objects of virtual anatomy are displayed.

14. The method according to claim 10, further comprising:
capturing, in the memory of the console, eye movements of a wearer using one or more eye-tracking cameras coupled to the frame of the alternative-reality headset; and
processing the eye movements with an eye-movement algorithm to identify a focus of the wearer for selecting or enhancing the objects of virtual anatomy corresponding to the focus of the wearer.

15. The method according to claim 10, further comprising:
capturing in the memory of the console gestures of the wearer using one or more patient-facing cameras coupled to the frame of the alternative-reality headset; and
processing the gestures with a gesture-command algorithm to identify gesture-based commands issued by the wearer for execution thereof by the alternative-reality headset.

16. The method according to claim 10, further comprising:
capturing in the memory of the console audio of the wearer using one or more microphones coupled to the frame of the alternative-reality headset; and
processing the audio with an audio-command algorithm to identify audio-based commands issued by the wearer for execution thereof by the alternative-reality headset.

17. The method according to claim 10, wherein each magnetic sensor of the array of magnetic sensors is embedded within a rigid frame for the housing, the magnetic sensors having a fixed spatial relationship to each other.

18. The method according to claim 17, further comprising:
- generating a magnetic field with a magnetic-field generator; and
- determining the spatial relationship of each magnetic sensor of the array of magnetic sensors to another magnetic sensor from the magnetic-sensor signals produced by the array of magnetic sensors while in the presence of the generated magnetic field.

* * * * *